(12) United States Patent
Rennecker (10) Patent No.: US 9,062,834 B2
(45) Date of Patent: Jun. 23, 2015

(54) ILLUMINATED DEVICE FOR ELECTRICIAN SNAKE OR FISHING SYSTEM

(71) Applicant: Christopher D. Rennecker, Fort Wayne, IN (US)

(72) Inventor: Christopher D. Rennecker, Fort Wayne, IN (US)

(73) Assignee: Top-Notch Concepts LLC, Fort Wayne, IN (US)

( * ) Notice: Subject to any disclaimer, the term of this patent is extended or adjusted under 35 U.S.C. 154(b) by 162 days.

(21) Appl. No.: 13/720,148

(22) Filed: Dec. 19, 2012

(65) Prior Publication Data

US 2013/0155668 A1    Jun. 20, 2013

Related U.S. Application Data

(60) Provisional application No. 61/577,824, filed on Dec. 20, 2011.

(51) Int. Cl.
*F21V 33/00* (2006.01)
*F21L 4/04* (2006.01)
*A61C 1/08* (2006.01)
*B25B 23/18* (2006.01)
*A61B 1/06* (2006.01)
*H02G 1/08* (2006.01)
*F21Y 101/02* (2006.01)

(52) U.S. Cl.
CPC . *F21L 4/04* (2013.01); *A61C 1/088* (2013.01); *B25B 23/18* (2013.01); *A61B 1/0684* (2013.01); *F21V 33/008* (2013.01); *F21Y 2101/02* (2013.01); *H02G 1/083* (2013.01)

(58) Field of Classification Search
CPC ............ G02B 23/2469; F21V 33/0084; A61B 1/0661; A61B 1/0684; A61C 1/088; F21W 2131/202; B25B 23/18
USPC .......................... 362/555, 572–574, 119, 120
See application file for complete search history.

(56) References Cited

U.S. PATENT DOCUMENTS

| | | |
|---|---|---|
| 2,176,620 A | 10/1939 | Beam |
| 3,017,499 A | 1/1962 | Fore |
| 3,074,196 A | 1/1963 | Bronson |
| 3,182,960 A | 5/1965 | French |
| 3,336,469 A | 8/1967 | Barnes |
| 3,370,356 A * | 2/1968 | Jend ............................... 33/639 |
| 4,026,059 A | 5/1977 | Ochs |

(Continued)

OTHER PUBLICATIONS

CE Pro magazine, Robert Archer, Klein Device Illuminates Fishing Expeditions, http://www.cepro.com/article/print/klein_device_illuminates_fishing_expeditions/, Nov. 16, 2012.

(Continued)

*Primary Examiner* — Julie Bannan
(74) *Attorney, Agent, or Firm* — Bose McKinney & Evans LLP (57) ABSTRACT

An illumination device having a first housing member with a threaded stem and a second housing member with a threaded bore wherein the threaded stem and the threaded bore are positioned at opposite ends of the device when the housing members are coupled together. An electrical power source, which may take the form of a battery, is disposed within the device and a selectively activated light source, which may take the form of an LED, is operably coupled with the power source. In some embodiments, the light source is selectively activated and deactivated by relative rotation of the first and second housing members.

19 Claims, 5 Drawing Sheets

(56) References Cited

U.S. PATENT DOCUMENTS

| | | | |
|---|---|---|---|
| 4,039,142 A | 8/1977 | Smith | |
| 4,348,715 A | 9/1982 | Christensen et al. | |
| 4,480,295 A | 10/1984 | Shuster | |
| 4,523,259 A | 6/1985 | Dorsett et al. | |
| 5,152,598 A | 10/1992 | Schaffer | |
| 5,179,797 A | 1/1993 | Edwards et al. | |
| 5,440,297 A | 8/1995 | Bright | |
| 5,550,719 A | 8/1996 | Kuo | |
| 5,580,147 A * | 12/1996 | Salerno | 362/551 |
| 5,644,864 A | 7/1997 | Kelly | |
| 5,820,249 A | 10/1998 | Walsten et al. | |
| 5,921,673 A | 7/1999 | Habel et al. | |
| 6,030,090 A | 2/2000 | Huang | |
| 6,033,081 A | 3/2000 | Huang | |
| 6,428,180 B1 | 8/2002 | Karram et al. | |
| 6,443,729 B1 | 9/2002 | Watson | |
| 6,454,453 B1 | 9/2002 | Ambrosio | |
| 6,972,377 B2 | 12/2005 | Sawyer et al. | |
| 7,001,037 B1 * | 2/2006 | Shiao | 362/109 |
| 7,025,333 B1 | 4/2006 | Gianturco | |
| 7,150,448 B1 | 12/2006 | Swift | |
| 7,278,751 B2 | 10/2007 | Chang et al. | |
| 7,299,865 B1 | 11/2007 | Kocher | |
| 7,527,311 B2 | 5/2009 | Shih | |
| 7,824,054 B2 | 11/2010 | Rigsbee, Jr. et al. | |
| 8,544,822 B2 | 10/2013 | Forthman | |
| 2007/0223214 A1 * | 9/2007 | Yen | 362/118 |
| 2008/0026647 A1 | 1/2008 | Boehnlein et al. | |
| 2009/0257221 A1 | 10/2009 | Patterson | |
| 2010/0328924 A1 | 12/2010 | Nissen | |

OTHER PUBLICATIONS

Illuminated Fish Rod Tip, Klein Tools, inc., unknown date, Lincolnshire, IL (1 page brochure).

"Fishing" Greenlee Product Catalog, p. 131-144, Greenlee, A Textron Company, unknown date.

* cited by examiner

ILLUMINATED DEVICE FOR ELECTRICIAN SNAKE OR FISHING SYSTEM

CROSS REFERENCE TO RELATED APPLICATIONS

This application claims priority under 35 U.S.C. 119(e) of U.S. provisional patent application Ser. No. 61/577,824 filed on Dec. 20, 2012 entitled ILLUMINATED DEVICE FOR ELECTRICIAN SNAKE OR FISHING SYSTEM the disclosure of which is hereby incorporated herein by reference.

BACKGROUND OF THE INVENTION

The present invention relates to electrician snakes or fishing systems which are used to "fish" wiring and cables through tight spaces such as insulated walls, drop ceilings and under floor spaces. More specifically, the present invention relates to an illuminated device which can be used with such tools.

When using such tools, an electrician will generally insert the snake or fishing device, e.g., a fish tape, into a tight space with very limited light. To successfully employ the tool, an additional source of light is beneficial. While known illumination devices exist which can be used to provide light in combination with an electrician's flexible snake or fishing system, such known devices generally replace one of the existing components of the tool, thereby duplicating a part already owned by the electrician and thus being unnecessarily expensive.

SUMMARY OF THE INVENTION

The present invention provides an illumination device which can be employed with existing electrician snakes or fishing systems without unnecessarily duplicating components of the electrician's pre-existing tool.

The invention comprises, in one form thereof, an illumination device having a first housing member with a threaded stem and a second housing member with a threaded bore wherein the threaded stem and the threaded bore are positioned at opposite ends of the device when the first and second housing members are coupled together. An electrical power source is coupled with the device and a selectively activated light source is operably coupled with the power source.

The invention comprises, in another form thereof, an illumination device having a first housing member with a threaded stem and a second housing member with a threaded bore wherein the first and second housing members are threadingly coupleable and the threaded stem and the threaded bore are positioned at opposite ends of the device when the first and second housing members are threadingly coupled together. A battery is disposed within the device and a light source is operably coupled with the power source wherein the light source is selectively activated and deactivated by relatively rotating the first and second housing members.

The light source may take the form of a light emitting diode ("LED"). In some embodiments, the threaded stem and the threaded bore have a common diameter and a common pitch whereby the threaded stem and threaded bore define a first thread configuration and are threadingly engageable.

In some embodiments, the first and second housing members are at least partially formed of anodized aluminum and at least one of the first and second housing members defines a portion of an electrical circuit operably coupling the electrical power source and the light source. The housing member forming a portion of the circuit includes first and second non-anodized aluminum surfaces forming electrical contact surfaces for electrically communicating with the electrical circuit. The first non-anodized aluminum surface is selectively engageable with an opposing electrical contact surface by relative rotation of the first and second housing members to thereby open and close the electrical circuit coupling the electrical power source and the light source.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION OF THE INVENTION

An exemplary illuminated device 20 is depicted in FIGS. 1A-3. Device 20 includes a first housing member 22 also referred to herein as a base member and a second housing member 24 which is also referred to herein as a cap member.

A conventional bullet shaped fitting 26 attached to cap member 24 is also shown in FIGS. 1A-2B. Cap member 24 is shown in greater detail in FIGS. 4-8 while base member 22 is best seen in FIGS. 9-12.

Cap 24 has a front threaded bore 28 and a rear bore 30. In the exemplary embodiment, front bore 28 has a non-threaded section 32 and a threaded section 34. Similarly, rear bore 30 also includes a non-threaded section 36 and a threaded section 38 in the exemplary embodiment. Front bore 28 is adapted to receive the threaded stem 40 of a conventional fitting 26. Threaded stems 40 can be seen in FIG. 16 which illustrates two additional conventional fittings 26A and 26B.

Cap 24 also includes a plurality of light passages 42. The exemplary cap 24 has three equidistantly spaced passages 42 which are positioned 120 degrees apart relative to the co-linear centerlines of front and rear bores 28, 30. The exterior surface of cap 24 defines a forward section 44 having a generally cylindrical shape, a rear section 48 also having a generally cylindrical shape but with a larger diameter than the forward section 44 and an intermediate shoulder section 46 extending between the forward 44 and rear 48 sections. Light passages 42 extend in a forward direction from the rear bore 30 and define openings 50 in shoulder section 46. As discussed in greater detail later, a light source is disposed in each of the light passages 42 and project light through an associated passage 42 and opening 50. By positioning openings 50 at a position radially outwardly of threaded bore 28 to facilitate the emission of light beyond threaded bore 28 and a fitting mounted therein in a direction parallel with axis 21.

Turning now to FIGS. 9-12, base member 22 will be discussed. Base 22 includes a rearwardly extending threaded stem 52. Stem 52 includes a large diameter cylindrical section 54 and a smaller diameter section 56 having a non-threaded portion 58 and a distal threaded portion 60. The small diameter portion 56 of threaded stem 52 corresponds to the standardized threaded stems of conventional fittings 26, 26A and 26B. In other words, threaded stem 52 could be threadingly engaged with threaded front bore 28. Practically, what this means is that on a conventional electrician's fish tape or similar tool, the conventional fitting can be removed from the tape and device 20 threaded into the receptacle for the fitting with the fitting then being threaded into front bore 28 of device 20.

When using device 20, stem 52 will not be threadingly engaged with bore 28, the threads of bore 28 and stem 52 are simply capable of such engagement in the illustrated embodiment. When using device 20, stem 52 and bore 28 will be disposed opposite each other. Both stem 52 and bore 28 are concentrically disposed relative to axis 21. Axis 21 also defines the axis of relative rotation between housing members 22, 24 when housing members 22, 24 are threadingly engaged.

Extending forward from threaded stem 52 is a hollow generally cylindrical portion 62 with a radial flange 64 near stem 52 and a blind bore 66 which defines an opening 68 on the end opposite stem 52. The radially exterior surface of cylindrical portion 62 includes an annular O-ring groove 68 and threads 70. When assembling device 20, cylindrical portion 62 is inserted into rear bore 30 of cap 24 with threads 70 engaging threaded portion 38 of bore 30. An O-ring 69 seated in groove 68 engages non-threaded portion 36 of rear bore 30 when cap 24 is secured on base 22. Flange 64 acts as a stop and limits the extent to which cap 24 can be rotated onto base 22. Flange 64, with its inclined surface 65, also acts to inhibit cap 24 from catching on items when device 20 is being pulled through a space in the direction of stem 52.

In the illustrated embodiment, both cap member 24 and base member 22 are formed out of aluminum. The exterior surface of base member 22 is anodized except for the bottom surface 72 of bore and a circular ring-shaped non-anodized surface 74 on the forward end 76 of base 22. These two non-anodized surfaces allow base member 22 to act as an electrical conductor to transmit electrical power from a battery 78 disposed in bore 66 to a printed circuit board assembly 80. Those portions of base member 22 which have been anodized have an oxide layer which acts as an electrical insulator and limits the ability of make an electrical connection to base member 22 to non-anodized surfaces 72, 74. The entire exterior surface of cap 24 can also be anodized if desired. The oxide layer formed by anodizing process not only acts as an electrically insulating layer but also provides corrosion resistance.

Figures 1A, 1B, 1C, 1D, 2B:
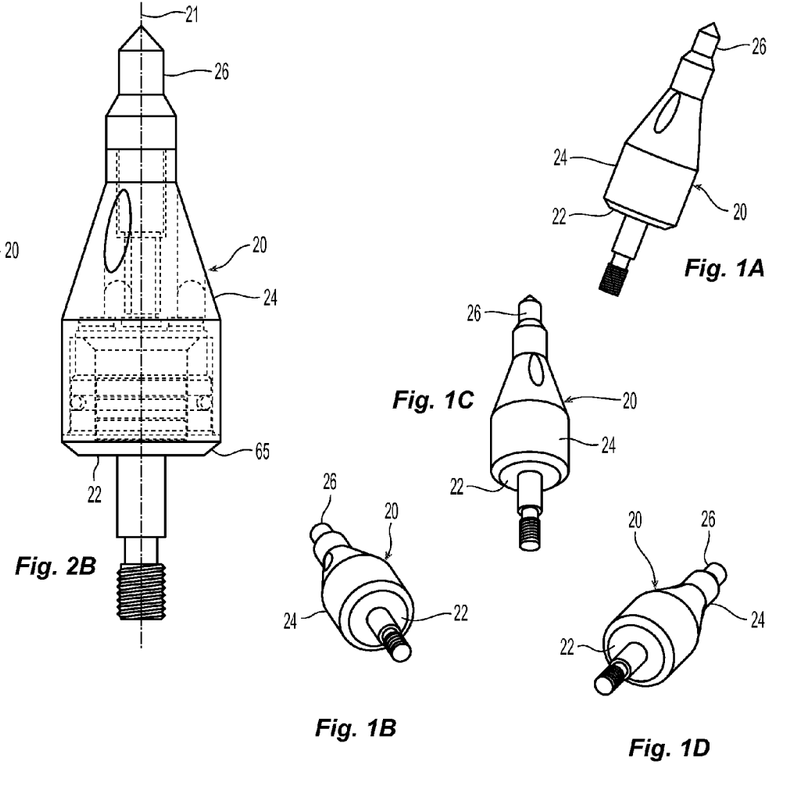
FIG. 1A is a perspective view of an exemplary embodiment with a conventional fitting attached thereto.
FIG. 1B is another perspective view of the exemplary embodiment and fitting of FIG. 1A.
FIG. 1C is another perspective view of the exemplary embodiment and fitting of FIG. 1A.
FIG. 1D is another perspective view of the exemplary embodiment and fitting of FIG. 1A.
FIG. 2B is another side view of the exemplary embodiment with a conventional fitting attached thereto.
Figure 2A:
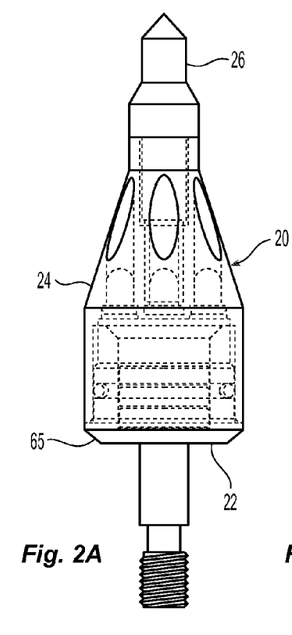
FIG. 2A is a side view of the exemplary embodiment with a conventional fitting attached thereto.
Figure 3:
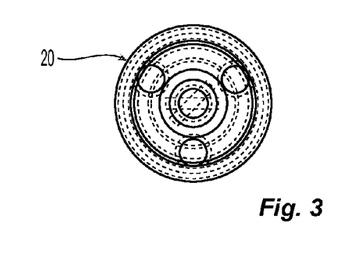
FIG. 3 is an end view of the exemplary embodiment.
Figure 4:
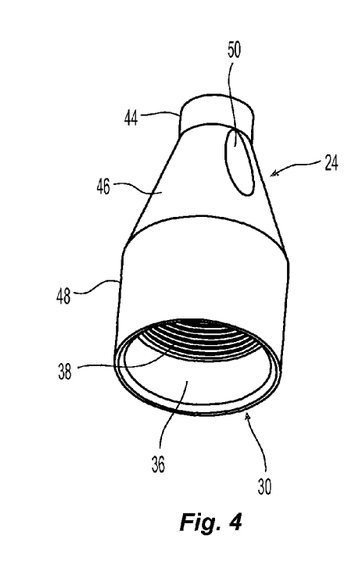
FIG. 4 is a perspective view of the cap.
Figure 5:
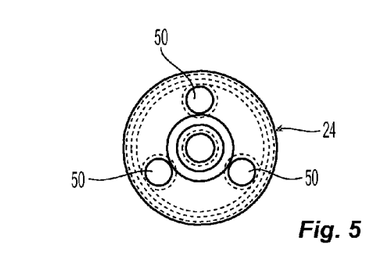
FIG. 5 is an end view of the cap.
Figure 6:
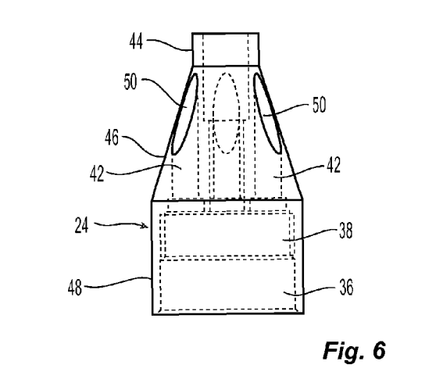
FIG. 6 is a side view of the cap.
Figure 7:
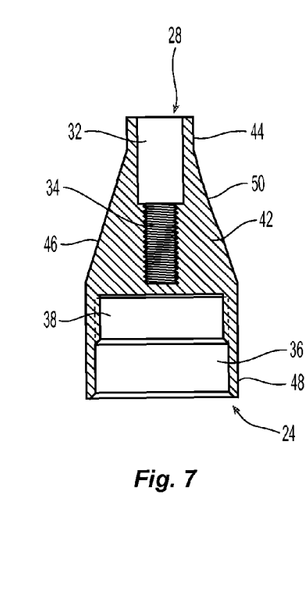
FIG. 7 is a cross sectional view taken along line A-A of FIG. 6.
Figure 8:
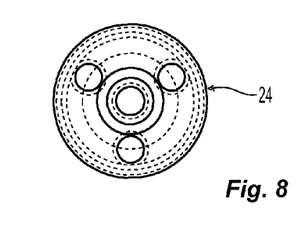
FIG. 8 is another end view of the cap.
Figure 9:
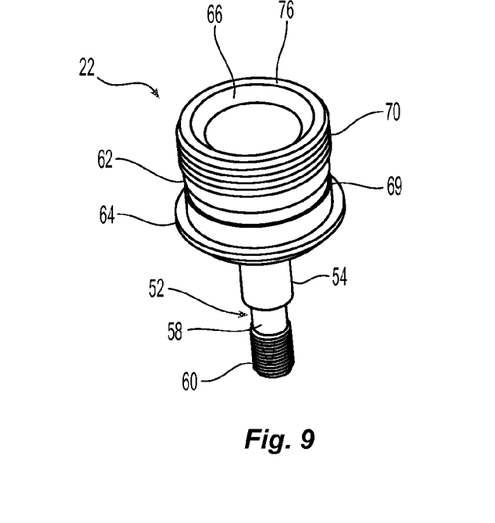
FIG. 9 is a perspective view of the base.
Figure 10:
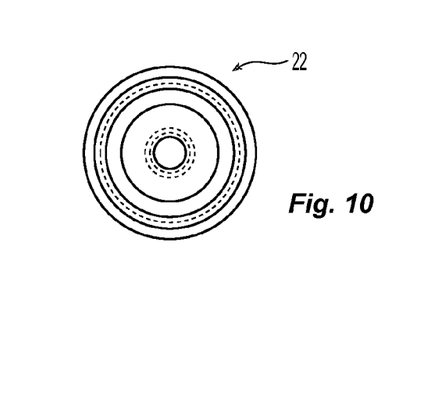
FIG. 10 is an end view of the base.
Figure 11:
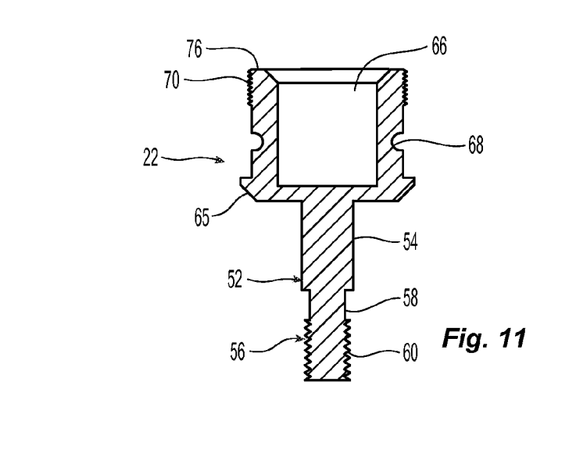
FIG. 11 is a cross sectional view taken along line A-A of FIG. 10.
Figure 12:
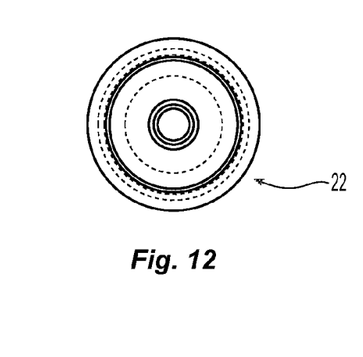
FIG. 12 is another end view of the base.
Figure 13A:
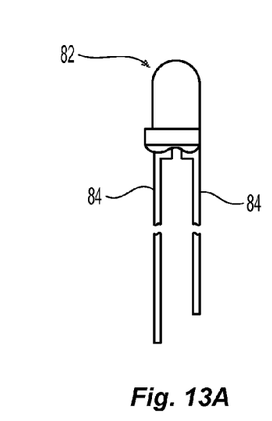
FIG. 13A is a side view of an LED light.
Figure 13B:
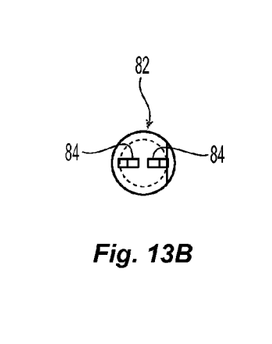
FIG. 13B is an end view of the LED light.
Figure 14A:
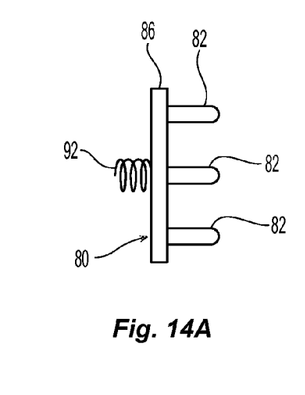
FIG. 14A is a side view of a circuit board.
Figure 14B:
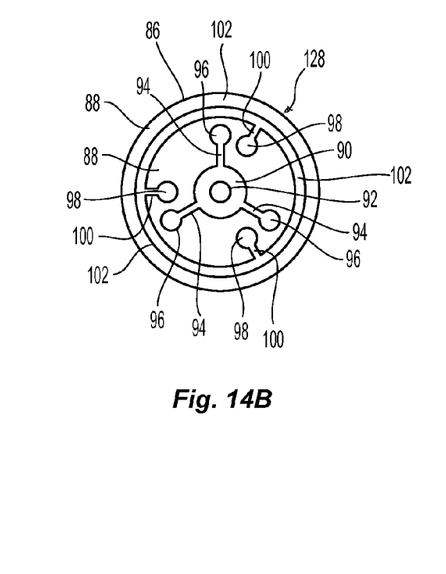
FIG. 14B is an end view of the circuit board.

Circuit board assembly 80 forms a part of electrical circuit 128 which couples battery 78 with LED lights 82 and is best understood with reference to FIGS. 14A and 14B. Light emitting diodes (LED lights) 82 are shown in FIGS. 13A and 13B and have electrical leads 84 extending outwardly therefrom. The exemplary embodiment has three LED lights 82 which mounted on circuit board 86. Circuit board 86 is positioned in rear bore 30 of cap 24 and LED lights 82 are positioned on board 86 so that each of the LED lights 82 project into one of the light passages 42. FIG. 14B shows the bottom of circuit board 86 which faces base member 22. This surface of board 86 includes non-electrically conductive portions 88 and conductive traces. The conductive traces include a central trace 90 onto which an electrically conductive spring 92 is soldered. Spring 92 can be engaged with one surface of battery 78 to thereby form an electrical connection therewith as discussed in greater detail below.

Three conductive traces 94 extend outward from central trace 90 and are electrically connected, e.g., by soldering, with a lead 84 from one of the LED lights 82 extending through board 86 at locations 96. The opposite lead 84 of each of the LED lights 82 also extends through board 86 is connected at a location 98. A conductive trace 100 extends from locations 98 to an annular ring shaped conductive trace 102 located near the outer periphery of circular board 86. When attaching LED lights 82 to board 86, all of the cathodes will be connected at locations 96 and all of the anodes being connected at locations 98. Alternatively, all of the cathodes can be connected at locations 98. Although the illustrated embodiment utilizes an LED light that has leads extending through the thickness of circuit board 86, surface mount LED lights can also be employed with the present invention. Surface mount LED lights do not have leads which extend through the circuit board and, instead, are soldered to the circuit board on the same surface from which the LED extends. When using surface mount LED lights, vias or other suitable means can be employed to provide an electrical connection between the surface mount LED lights and conductive traces 96, 98 located on the opposite side of board 86.

Figure 15A:
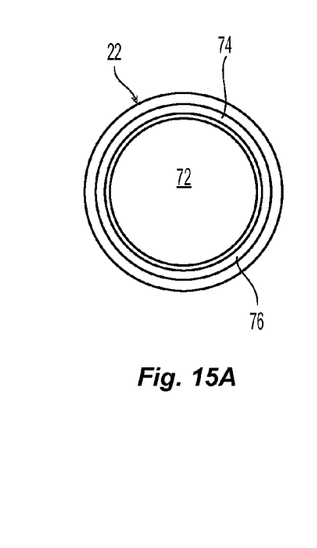
FIG. 15A is an end view of the base.
Figure 15B:
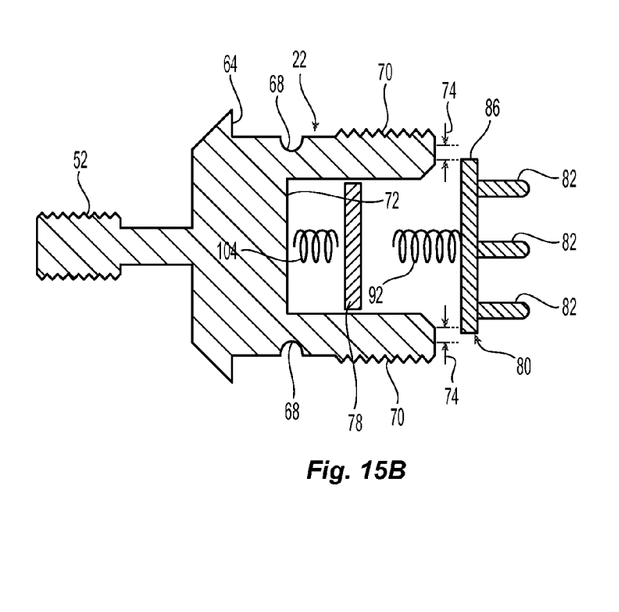
FIG. 15B is a schematic cross sectional view of the base, a battery and the circuit board.

The completion of the electrical circuit to illuminate LED lights 82 can be understood with reference to FIGS. 15A and 15B in addition to FIG. 14B. When cap 24 is screwed down on base 22, cap 24 presses board 86 against forward edge 76 of base 22 and thereby also brings annular trace 102 into contact with non-anodized surface 74. Spring 92 is simultaneously engaged with battery 78. The opposite side of disk shaped battery 78 engages the bottom, non-anodized surface 72 of bore 30. FIG. 15B shows an optional, electrically conductive spring 104 that can be positioned between surface 72 and battery 78. The engagement of spring 92 with battery 78 and engagement of annular trace 102 with non-anodized surface 74 completes the electrical circuit to thereby light LED lights 82.

As evident from the above description, housing member 22 thus forms a portion of electrical circuit 118 with two non-anodized aluminum surfaces 72, 74 forming electrical contact surfaces for electrically communicating with the remainder of electrical circuit 118. In this embodiment, surface 74 is selectively engageable with an opposing electrical contact surface, i.e., annular trace 102 in the illustrated embodiment, by relative rotation of housing members 22, 24 to thereby open and close electrical circuit 118 which couples battery 78 with LED lights 82. Alternative embodiments could position the electrical contact surfaces on housing member 22 differently or provide such surfaces with a different configuration. Still other embodiments might not utilize either of the housing members 22, 24 as a part of the electrical circuit 118.

Although only a single battery 78 is employed in the illustrated embodiment, alternative embodiments may utilize a plurality of stacked batteries 78 or alternative arrangements of batteries to provide electrical power to LED lights 82.

In the illustrated embodiment, spring 92 not only provides electrical communication between battery 78 and printed circuit board 86, spring 92 also biases printed circuit board 86, and annular trace 102 located thereon, away from non-anodized surface 74 to thereby maintain electrical circuit 128 in an open position. LED lights 82 will be deactivated when circuit 128 is open. To close circuit 128 and activate LED lights 82, housing members 22, 24 are relatively rotated to threadingly engage housing members 22, 24, i.e., tighten housing members 22, 24, and thereby bring surface 74 into contact with trace 102 and close electrical circuit 128 and activate LED lights 82. Alternative arrangements can also be used to open and close circuit 128. For example, instead of relying upon the tightening of housing members 22, 24 to close circuit 128, trace 102 and contact surface 74 may have a non-annular configurations whereby they are brought into contact only when housing members 22, 24 are at a particular relative angular position. Moreover, in such an embodiment, the springs may be rearranged to continually bias trace 102 toward contact surface 74 instead of away from contact surface 74. Many other alternative configurations of contact surfaces to open and close circuit 128 and selectively activate LED lights 82 can also be employed. For example, an externally accessible switch could also be employed with device 20.

Returning to a discussion of illustrated electrical circuit 128 which couples LED lights 82 with battery 78, one pole of battery 78 is in electrical communication with spring 92 which communicates electrical power to central trace 90 from which it is communicated via traces 94 to a lead 84 of each of the LED lights 82 at locations 96. The circuit continues through each LED light 82 to the opposite lead 84 which is connected at location 98 to conductive traces 100. Conductive traces 100 are in communication with annular trace 102 which, in turn, is in communication with non-anodized surface 74. The body of the base member 22 provides for the communication of electrical current between non-anodized surface 74 and non-anodized surface 72. Surface 72 is then either in direct electrical communication with the opposite pole of battery 78 or in indirect communication via optional spring 104. In the illustrated embodiment, battery 78 is a manganese dioxide lithium coin battery, however, other types of batteries may also be used with device 20.

While the illustrated circuit board assembly 80 and other components of device 20 illustrate one manner of powering a light source alternative circuits could also be employed. For example, LED lights 82 could be connected in series instead of in parallel as depicted. Furthermore, more or fewer LED lights 82 than the depicted three LED lights 82 could be employed with device 20. For example, a single LED light 82 could be employed. With regard to optional spring 104, it is noted that this spring can be omitted. In some situations, however, spring 104 can provide an advantage by allowing the length of spring 92 to be reduced. By reducing the length of spring 92, spring 92 is less likely to become detached from board 86.

To deactivate LED lights 82, cap 24 is partially unscrewed until the electrical contact between surface 74 and annular trace 102 is broken. Spring 92 biases board 86 away from base 22 and thereby minimizes the extent to which cap 24 must be unscrewed to deactivate LED lights 82 and also maintains board 86 in a spaced apart position from forward edge 76 to maintain LED lights 82 in a de-activated condition after partially unscrewing cap 24. To reactivate LED lights 82, cap 24 is simply turned in the opposite direction to bring annular trace 102 once again into contact with surface 74. It is noted that the use of an O-ring 69 disposed in groove 68 between base 22 and cap 24 and engaging each of base 22 and cap 24 provides some resistance to the relative rotation of base 22 and cap 24 and thereby helps to maintain the base 22 and cap 24 in the selected rotational position.

Figure 16:
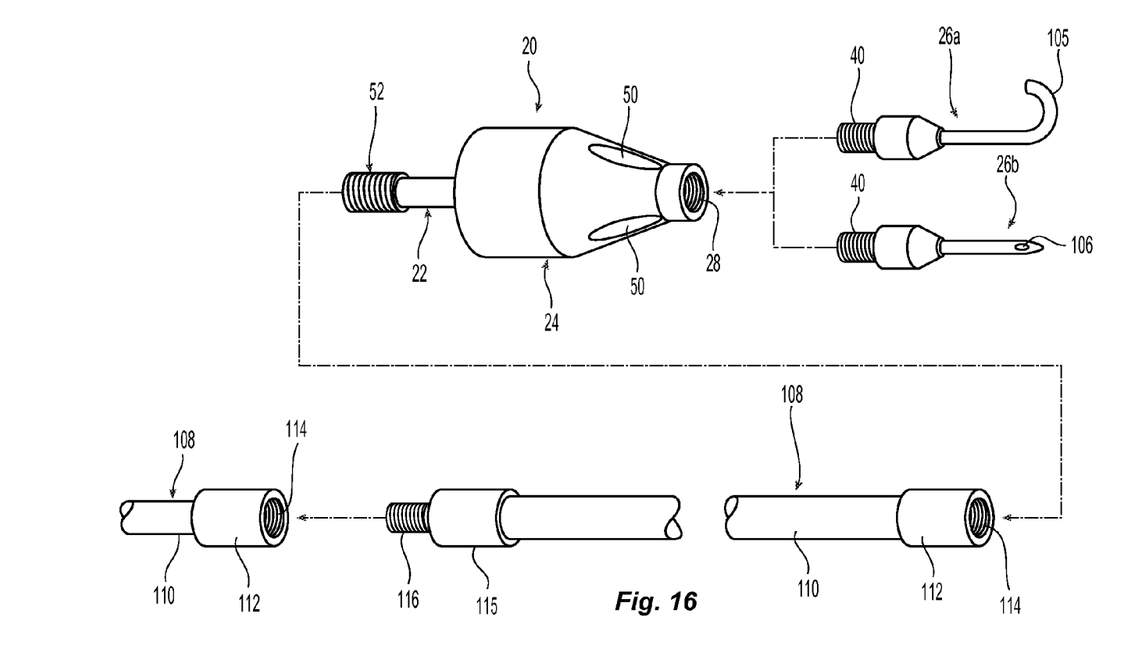
FIG. 16 is an exploded view showing the exemplary embodiment device with elongate rods and conventional fittings.

Turning now to FIG. 16, the use of device 20 will now be discussed. Conventional fitting 26A has a threaded stem 40 which is securable within threaded bore 28 on cap 24 and a hook portion 105 that can be used to pull cables, wires or other items through insulated walls, drop ceilings and other similar spaces. An alternative conventional fitting 26B is also shown in FIG. 16 and includes a threaded stem 40 that can be secured within bore 28 and has a projection with an eyelet 106 which can be used when installing cables, wires and other similar items through tight spaces.

Two elongate members 108 are also shown in FIG. 16. Elongate members 108 have a fiberglass rod 110 with a ferrule 112 having a threaded bore 114 at one end and a ferrule 115 with a threaded stem 116 on the other end. The elongate members 108 have an extended length, e.g., one or more meters, and take the form of flexible rods which can be joined end-to-end and thereby form a tool of the desired total length. A conventional fitting, e.g., fitting 26, 26A or 26B, is typically attached to the threaded bore 114 of a ferrule 112 located at one end of the assembly or elongate members 108. When using device 20, threaded stem 52 on base 22 is engaged with the threaded bore 114 on ferrule 112 located at one end of the assembly of elongate members 108 and the selected fitting is secured to cap 24 by engaging the threaded stem 40 of the fitting with threaded bore 28. Elongate members 108 are commercially available from Greenlee Textron Inc. under the name Fish Stix®. Conventional fittings for use with elongate members 108 are also available from Greenlee Textron Inc.

When employing the assembled elongate members 108, illumination device 20 and selected fitting, cap 24 is twisted to activate the LED lights 82 before inserting the fitting end of the assemblage into the tight space. For example, the assemblage might be inserted into a drop ceiling with the LED lights 82 providing illumination near the attached fitting. The provision of illumination at the fitting end of the assemblage allows the user to more easily guide the fitting end of the assemblage to the desired location.

A variety of different electrician fishing sticks and tapes are commercially available and with which device 20 can be used. One complicating factor is that the different manufacturers of these devices often employ different thread configurations. In this regard, it is noted that the helical thread of a "screw" type attachment as used with threaded bore 28 and threaded stem 52 requires that the two parts, male and female, being threadingly engaged have corresponding diameters and thread pitches for the parts to be properly threadingly engaged. When both the male and female parts have a common thread configuration with corresponding diameters and pitches the male and female parts can be threadingly engaged. When either the diameter or thread pitch of the male and female parts are not corresponding the male and female parts do not have a common thread configuration and will not be able to be properly threaded into engagement. To accommodate the different thread configurations used by the different manufacturers, a multiplicity of devices 20 can be manufactured with each of the different models of device 20 having threaded bores 28 and threaded stems 52 matching the particular thread configuration of a different manufacturer.

Figure 18:
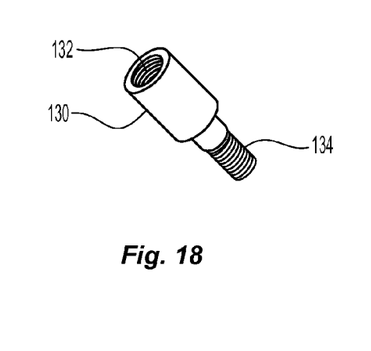
FIG. 18 is a perspective view of an adapter.

Alternatively, an adapter 130 shown in FIG. 18 can be used. Adapter 130 has a threaded bore 132 and a threaded stem 134 disposed opposite bore 132. Bore 132 has a first thread configuration while threaded stem 134 has a different, incompatible, second thread configuration. Typically, a user will acquire a device 20 suited for the electrician fish sticks or tapes that the user intends to use. If the user then has a need to employ a different electrician fish stick or tape having a different thread configuration, the user could still employ the same device 20 using either one or two adapters 130. Generally, the user will have fittings, e.g., fitting 26, that are compatible with the device 20 in which case a single adapter 130 can be used. The adapter 130 will have a threaded bore 132 with the same thread configuration as device 20 whereby stem 52 of device 20 can be engaged with adapter 130. The threaded stem 134 of adapter 130 will have a different thread configuration adapted to engage the threaded bore of the alternate fishing stick or tape. If necessary, a second adapter could be employed to adapt fittings to the device 20, however, it will generally be unnecessary to employ an adapter for the fittings.

Device 20 can, however, be provided with multiple adapters 130 for a different purpose. Each of the multiple adapters 130 would have a threaded bore 132 with the same thread configuration for engaging the stem 52 of a single device 20 but have threaded stems 134 with different thread configurations. This would allow for the interchange of the different adapters 130 and thereby allow device 20 to be used with a corresponding number of differently threaded electrician fishing sticks and tapes. In other words, a specific adapter 130 can be provided to adapt device 20 to the specific thread configuration of each manufacturer.

As mentioned above, threaded bore 28 and threaded stem 52 are threadingly engageable, in other words, the threads of bore 28 and stem 52 have a common configuration with both a common diameter and a common thread pitch. While it will generally be advantageous for device 20 to have a threaded bore 28 and stem 52 with a common thread configuration, alternative embodiments could employ a bore 28 and stem 52 having different thread configurations to adapt device 20 for a particular application.

Figure 17:
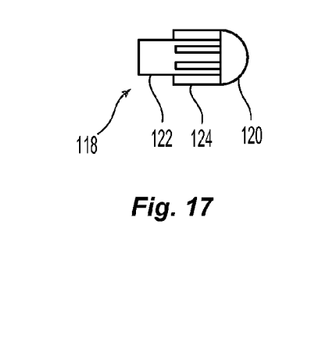
FIG. 17 is a side view of a light pipe that can be used with the illustrated illumination device.

It is further noted that it is also possible to position a light pipe or similar device in one or more of the light passages 42 to enhance or alter the illumination provided by LED lights 82. For example, to provide a more diffuse and general illumination near the attached fitting, a light pipe 118 as depicted in FIG. 17 can be employed. The use of such light pipes with LED lights is well known and such light pipes 118 are typically formed out of a clear polymeric material. The light pipe 118 illustrated in FIG. 17 includes a hemispherical head 120, a cylindrical stem 122 and ribs 124. A light pipe 118 can be positioned in each passage 42 in cap 24 with head 120 projecting beyond opening 50. Light pipe 118 facilitates the communication of light from LED light 82 to the surrounding area to thereby limit the extent to which LED lights 82 illuminate the interior of device 20 instead of the surrounding area. Hemispherical head 120 also causes the light transmitted through light pipe 118 from LED light 82 to provide a generally diffuse illumination which illuminates the general area around the fitting instead of a more highly concentrated beam of light. The removal of pipes 118 or use of alternative light pipes allows for the provision of more concentrated light when such concentrated light is desired. Another alternative for providing more generalized lighting is to form all or a substantial portion of housing member 24 out of a clear polymeric material.

If desired, housing member 22 could also be formed out of or incorporate a clear material to provide for "rearward" directed lighting having either a concentrated or diffuse pattern. A concentrated lighting pattern could be provided by the use of isolated openings while a diffuse pattern could be provided by the use of a light pipe or by employing a clear material in the construction of housing member 22 to provide a larger area through which light may exit member 22. In this regard, it is noted that a clear plastic housing member could be overmolded about metallic bodies such as an electrically conductive element or have such metallic bodies secured within the housing member.

As those having ordinary skill in the art will recognize still other variations on the disclosed device 20 can be employed. For example, instead of housing portions of electrical circuit 118 in both housing member 22 and housing member 24, all portions of the electrical circuit 118 could be housed in only one of the two members, e.g., cap member 24. Moreover, instead of using two housing members, a single housing member or more than two housing members could be used when forming device 20.

It is also noted that the disclosed embodiment employs a light source 82 in the form of an LED light and the use of an LED light will generally be advantageous. Other light sources, however, such as a small incandescent bulb, could alternatively be used. Moreover, while the disclosed power source is a battery and the use of a battery will generally be advantageous, in some specialized applications, e.g., applications where the tool on which device 20 is mounted carry a source of electrical power, it may be suitable for device 20 to employ an alternative power source such as an external electrical power source.

While this invention has been described as having an exemplary design, the present invention may be further modified within the spirit and scope of this disclosure. This application is therefore intended to cover any variations, uses, or adaptations of the invention using its general principles.

What is claimed is:

1. An illumination device comprising:
    a first housing member having a threaded stem;
    a second housing member having a threaded bore wherein the threaded stem and the threaded bore are positioned at opposite ends of the device when the first and second housing members are coupled together and wherein the threaded bore and the threaded stem have a common diameter and a common pitch;
    an electrical power source coupled with the device; and
    a selectively activated light source operably coupled with the power source.

2. The device of claim 1 wherein the threaded stem and the threaded bore are concentrically disposed relative to a common axis and wherein the light source emits light from the second housing member at a location radially outwardly of the threaded bore.

3. The device of claim 2 wherein the second housing defines at least one opening through which the light source emits light.

4. The device of claim 2 wherein the second housing comprises a clear material through which the light source emits light.

5. The device of claim 1
wherein the light source is selectively activated and deactivated by relatively rotating the first and second housing members.

6. The device of claim 5 wherein the first and second housing members are threadingly engaged.

7. The device of claim 6 wherein the electrical power source comprises a battery and the light source comprises an LED and wherein relative rotation of the first and second housing members opens and closes an electrical circuit operably coupling the battery and the LED and thereby selectively activates the LED.

8. The device of claim 7 wherein at least one of the first and second housing members defines a portion of the electrical circuit operably coupling the battery and the LED.

9. An illumination device comprising:
a first housing member having a threaded stem;
a second housing member having a threaded bore wherein the threaded stem and the threaded bore are positioned at opposite ends of the device when the first and second housing members are coupled together;
an electrical power source coupled with the device;
a selectively activated light source operably coupled with the power source wherein the light source is selectively activated and deactivated by relatively rotating the first and second housing members;
wherein the first and second housing members are threadingly engaged;
wherein the electrical power source comprises a battery and the light source comprises an LED and wherein relative rotation of the first and second housing members opens and closes an electrical circuit operably coupling the battery and the LED and thereby selectively activates the LED;
wherein at least one of the first and second housing members defines a portion of the electrical circuit operably coupling the battery and the LED; and
wherein the first and second housing members are at least partially formed of anodized aluminum and wherein the at least one housing member defining a portion of the electrical circuit includes first and second non-anodized aluminum surfaces forming electrical contact surfaces for electrically communicating with the electrical circuit, the first non-anodized aluminum surface being selectively engageable with an opposing electrical contact surface by relative rotation of the first and second housing members to thereby open and close the electrical circuit coupling the battery and the LED.

10. The device of claim 9 further comprising an O-ring disposed between and engaging each of the first and second housing members.

11. The device of claim 9 wherein the threaded stem and the threaded bore have a common diameter and a common pitch whereby the threaded stem and threaded bore define a first thread configuration and are threadingly engageable.

12. The device of claim 11 further comprising an adapter having a second threaded bore and a second threaded stem disposed opposite the second threaded bore, wherein one of the second threaded bore and the second threaded stem defines a thread with the first thread configuration and is thereby engageable with one of the threaded stem and the threaded bore of the device and the other of the second threaded bore and the second threaded stem defines a thread having a second thread configuration that is incompatible with the threaded stem and threaded bore of the device.

13. The device of claim 12 wherein the second threaded bore is engageable with the threaded stem of the first housing member.

14. The device of claim 13 further comprising a second adapter defining a third threaded bore and a third threaded stem disposed opposite the third threaded bore, the third threaded bore being engageable with the threaded stem of the first housing member and the third threaded stem defining a third thread configuration incompatible with both the first and second thread configurations.

15. An illumination device comprising:
a first housing member a threaded stem;
a second housing member having a threaded bore wherein the first and second housing members are threadingly coupleable and the threaded stem and the threaded bore are positioned at opposite ends of the device when the first and second housing members are threadingly coupled together;
a power source comprising a battery disposed within the device;
a light source operably coupled with the power source wherein the light source is selectively activated and deactivated by relatively rotating the first and second housing members; and
wherein the threaded stem and the threaded bore have a common diameter and a common pitch whereby the threaded stem and threaded bore define a first thread configuration and are threadingly engageable.

16. The device of claim 15 wherein the second housing defines at least one opening through which the light source emits light.

17. The device of claim 15 wherein the second housing comprises a clear material through which the light source emits light.

18. The device of claim 15 wherein the first and second housing members are at least partially formed of anodized aluminum and wherein at least one of the first and second housing members defines a portion of an electrical circuit operably coupling the battery and the light source, the at least one housing member including first and second non-anodized aluminum surfaces forming electrical contact surfaces for electrically communicating with the electrical circuit, the first electrical contact surface being selectively engageable with an opposing electrical contact surface by relative rotation of the first and second housing members to thereby open and close the electrical circuit coupling the battery and the light source.

19. The device of claim 18 wherein the relative rotation of the first and second housing members defines an axis and the threaded bore and the threaded stem are concentrically disposed relative to the axis; wherein the light source comprises an LED mounted on a printed circuit board defining the opposing electrical contact surface; and wherein the electrical circuit comprises a spring, the spring biasing the printed circuit board away from the first non-anodized aluminum surface and wherein the device further comprises an O-ring disposed between and engaging each of the first and second housing members.

* * * * *

UNITED STATES PATENT AND TRADEMARK OFFICE
CERTIFICATE OF CORRECTION

PATENT NO. : 9,062,834 B2
APPLICATION NO. : 13/720148
DATED : June 23, 2015
INVENTOR(S) : Christopher D. Rennecker Page 1 of 1

It is certified that error appears in the above-identified patent and that said Letters Patent is hereby corrected as shown below:

Specification
Col. 1, line 9, the year "2012" should read --2011--.
Col. 4, line 22, the term "which" should read --which are--; line 38, the phrase "board 86 is" should read --board 86 and is--.
Claims
Col. 10, claim 15, line 2, the phrase "member a" should read --member having a--.

Signed and Sealed this
Twelfth Day of April, 2016

Michelle K. Lee
*Director of the United States Patent and Trademark Office*